United States Patent
Mahal et al.

(10) Patent No.: US 10,905,899 B2
(45) Date of Patent: Feb. 2, 2021

(54) APPLICATORS SUITABLE FOR BRACHYTHERAPY AND METHODS USING SAME

(71) Applicant: YALE UNIVERSITY, New Haven, CT (US)

(72) Inventors: Amandeep Mahal, New Haven, CT (US); James Yu, New Haven, CT (US); Shari Damast, New Haven, CT (US); Rajwant Mahal, New Haven, CT (US)

(73) Assignee: Yale University, New Haven, CT (US)

( * ) Notice: Subject to any disclaimer, the term of this patent is extended or adjusted under 35 U.S.C. 154(b) by 283 days.

(21) Appl. No.: 15/940,219

(22) Filed: Mar. 29, 2018

(65) Prior Publication Data
US 2018/0289978 A1  Oct. 11, 2018

Related U.S. Application Data

(60) Provisional application No. 62/478,341, filed on Mar. 29, 2017.

(51) Int. Cl.
*A61N 5/10* (2006.01)
*A61B 17/42* (2006.01)

(52) U.S. Cl.
CPC .......... *A61N 5/1016* (2013.01); *A61B 17/42* (2013.01)

(58) Field of Classification Search
CPC .............................. A61N 5/1016; A61N 17/42
USPC ........................................................ 600/1–8
See application file for complete search history.

(56) References Cited

U.S. PATENT DOCUMENTS

| | | | | |
|---|---|---|---|---|
| 4,244,357 A * | 1/1981 | Morrison | ............. | A61N 5/1016 600/6 |
| 5,562,594 A * | 10/1996 | Weeks | ................. | A61N 5/1016 600/3 |
| 6,390,968 B1 * | 5/2002 | Harmon | ............... | A61N 5/1016 600/6 |
| 9,132,282 B2 * | 9/2015 | Makel | .................. | A61N 5/1016 |
| 2006/0173235 A1 | 8/2006 | Lim et al. | | |
| 2009/0234178 A1 * | 9/2009 | Lebovic | ................ | A61N 5/1016 600/6 |
| 2010/0145132 A1 * | 6/2010 | Isham | ................ | A61B 17/4241 600/7 |
| 2011/0257459 A1 | 10/2011 | Sutton et al. | | |

(Continued)

FOREIGN PATENT DOCUMENTS

GB        530318 A       12/1940

OTHER PUBLICATIONS

Cunha , et al., "Evaluation of PC-ISO for customized, 3D Printed, gynecologic 192-Ir HDR brachytherapy applicators" J Appl Clin Med Phys. 16(1), Jan. 2015, 5168.

*Primary Examiner* — Navin Natnithithadha
*Assistant Examiner* — Sunita Reddy
(74) *Attorney, Agent, or Firm* — Saul Ewing Arnstein & Lehr LLP; Kathryn Doyle; Domingos J. Silva

(57) ABSTRACT

The invention provides a two-step tapered applicator, which can be used to deliver high-dose-rate vaginal brachytherapy to a female patient's vagina post-hysterectomy. In certain embodiments, once inserted through the female patient's vaginal opening (or introitus), the applicator of the invention causes less physical discomfort to the female patient than currently available applicators. In other embodiments, the applicator is used in a female patient whose vaginal apex is larger in diameter than her vaginal introitus.

20 Claims, 8 Drawing Sheets

(56) References Cited

U.S. PATENT DOCUMENTS

| | | | | |
|---|---|---|---|---|
| 2012/0178983 A1* | 7/2012 | Benson | .............. | A61N 5/1015 |
| | | | | 600/7 |
| 2013/0109908 A1* | 5/2013 | Rahimian | ............ | A61N 5/1016 |
| | | | | 600/6 |
| 2014/0121443 A1* | 5/2014 | van Erp | ............... | A61N 5/1007 |
| | | | | 600/6 |
| 2014/0163664 A1* | 6/2014 | Goldsmith | ....... | A61B 17/12181 |
| | | | | 623/1.11 |
| 2015/0065784 A1* | 3/2015 | Fillmore | ............. | A61N 5/1014 |
| | | | | 600/6 |

* cited by examiner

APPLICATORS SUITABLE FOR BRACHYTHERAPY AND METHODS USING SAME

CROSS-REFERENCE TO RELATED APPLICATIONS

This application claims priority under 35 U.S.C. § 119(e) to U.S. Provisional Patent Application No. 62/478,341, filed Mar. 29, 2017, the contents of which are incorporated by reference herein in their entirety.

BACKGROUND OF THE INVENTION

Endometrial cancer is a cancer in the lining of the uterus or womb (endometrium), and may invade or spread to other parts of the body. Symptoms include non-menstrual vaginal bleeding, pain with urination or sexual intercourse, or pelvic pain. Endometrial cancer is an example of the broader class of uterine cancer, which further comprises cervical cancer, uterine sarcoma, and trophoblastic disease. More than 80% of cases of endometrial cancer are endometrioid carcinoma.

Endometrial carcinoma is the most common gynecologic malignancy in the U.S, and occurs generally after menopause. In 2016, about 60,050 new cases of endometrial cancer were recorded, resulting in about 10,470 deaths. If endometrial cancer is diagnosed at an early stage, the outcome is favorable. Overall five-year survival rate in the U.S. is greater than 80%. Endometrial cancer is generally associated with obesity, excessive estrogen exposure, high blood pressure and diabetes, with a small contribution from inherited genes.

Endometrial cancer is commonly diagnosed by endometrial biopsy or by taking samples during dilation and curettage. A pap smear is not typically sufficient to diagnose the disease.

A common treatment option for endometrial cancer is abdominal hysterectomy (total removal by surgery of the uterus), along with removal of the fallopian tubes and ovaries on both sides (bilateral salpingo-oophorectomy). Radiation therapy, chemotherapy or hormone therapy are also usually used.

Radiation therapy is commonly used in early-stage (stage I or II) endometrial cancer. It can be delivered through vaginal brachytherapy (VBT), which is a preferred route due to its reduced toxicity, or external beam radiotherapy (EBRT). Brachytherapy involves placing a radiation source in the organ affected (for endometrial cancer patients, a radiation source is placed directly inside the vagina). EBRT involves a beam of radiation aimed at the affected area from outside the body. VBT is used to treat any remaining cancer solely in the vagina, whereas EBRT can be used to treat remaining cancer elsewhere in the pelvis following surgery. VBT provides a better quality of life than EBRT.

Radiotherapy can also be used before surgery in certain cases. In fact, when there is evidence that the tumor has invaded the cervix, radiation can be given before a total hysterectomy is performed. VBT and EBRT can also be used, singly or in combination, when hysterectomy is not recommended. Unfortunately, both delivery methods of radiotherapy are associated with radiation side effects, particularly in the gastrointestinal tract.

There is thus a need in the art for novel devices that can be used to provide brachytherapy to female patients suffering from endometrial cancer in addition to other malignancies of the vagina, involving the vagina, or with potential to spread to the vagina. Such devices should provide a more comfortable experience for the patient, as well as maximize success rates for the procedure. The present invention fulfills this need.

SUMMARY OF THE INVENTION

The present invention provides a gynecological brachytherapy applicator. The present invention further provides a method of providing intravaginal brachytherapy to a female patient suffering from endometrial cancer or other malignancy of the vagina, involving the vagina, or with potential to spread to the vagina.

In certain embodiments, radiation is applied to at least a section of vaginal tissue of the female patient using the gynecological brachytherapy applicator as described herein.

In certain embodiments, the applicator comprises an elongated cylindrical body having a proximal end, a distal end, and a longitudinal axis that connects the proximal and distal ends of the cylindrical body. In certain embodiments, the cylindrical body of the applicator is sectioned along a plane spanning the longitudinal axis into first and second hemi-cylindrical bodies. In certain embodiments, the first and second hemi-cylindrical bodies can slide longitudinally with respect to each other along the sectioning plane. In certain embodiments, the surfaces of the first and second hemi-cylindrical bodies of the applicator are indented along the sectioning plane such that, when the proximal ends of the first and second hemi-cylindrical bodies are aligned and the distal ends of the first and second hemi-cylindrical bodies are aligned ("aligned applicator"), at least one single-opening channel is formed in the cylindrical body. In certain embodiments, the at least one channel is situated longitudinally along the cylindrical body and has its single opening to the proximal end of the elongated cylindrical body. In certain embodiments, in the aligned applicator, the diameter of the distal end is larger than the diameter of the proximal end. In certain embodiments, the cylindrical body has a tapering point along the longitudinal axis, wherein the diameter of the cylindrical body between the distal end and the tapering point is approximately the same, and the diameter of the cylindrical body gradually decreases between the tapering point and the proximal end.

In certain embodiments, the at least one single-opening channel is parallel to the longitudinal axis.

In certain embodiments, one of the at least one single-opening channels spans the longitudinal axis.

In certain embodiments, the at least one single-opening channel allows for insertion of a catheter into the cylindrical body.

In certain embodiments, the at least one single-opening channel ends about 3-7 mm away from the distal end of the cylindrical body.

In certain embodiments, the applicator comprises a material that is resistant to radiation and/or is thermoplastic.

In certain embodiments, the applicator comprises a polymer, wherein the polymer is at least one selected from the group consisting of fluoropolymer, natural latex, synthetic latex, polyurethane, polycarbonate, silicone, acetal or polyoxymethylene copolymer, heat stabilized polypropylene, polyphenylene oxide, polysulfone, polyether ether ketone, amorphous polyetherimide, polyphenolsulfone, and any combinations thereof. In certain embodiments, the polymer comprises a thermoplastic polycarbonate.

In certain embodiments, the surfaces of the first and second hemi-cylindrical bodies along the sectioning plane comprise a set of complementary indentations and projections that allow for the first and second hemi-cylindrical bodies to slide longitudinally with respect to each other along the sectioning plane.

In certain embodiments, the first hemi-cylindrical body comprises two indentations along the sectioning plane and the second hemi-cylindrical body comprises two complementary projections along the sectioning plane.

In certain embodiments, the first hemi-cylindrical body comprises a projection and an indentation along the sectioning plane and the second hemi-cylindrical body comprises a complementary indentation and a complementary projection, respectively, along the sectioning plane.

In certain embodiments, in the aligned applicator the diameter of the distal end is approximately 2-4 cm.

In certain embodiments, in the aligned applicator the diameter of the proximal end is approximately 1-3 cm.

In certain embodiments, the distance between the distal end and the tapering point is about 4-8 cm.

In certain embodiments, the distance between the proximal end and the tapering point is about 10-20 cm.

In certain embodiments, the first and second hemi-cylindrical bodies are secured to each other in the aligned applicator, so that the hemi-cylindrical bodies can no longer slide longitudinally with respect to each other along the sectioning plane.

In certain embodiments, the first and second hemi-cylindrical bodies are secured to each other using a part comprising a fastener, lock, pin, nail, clip, screw, strap, or various interlocking alignment tracks, wherein the part is attached to the cylindrical body in the vicinity of its proximal end.

In certain embodiments, at least one selected from the proximal end and the distal end is further tapered to an extremity of corresponding smaller diameter.

In certain embodiments, at least one selected from the proximal end and the distal end is further tapered to a round extremity.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
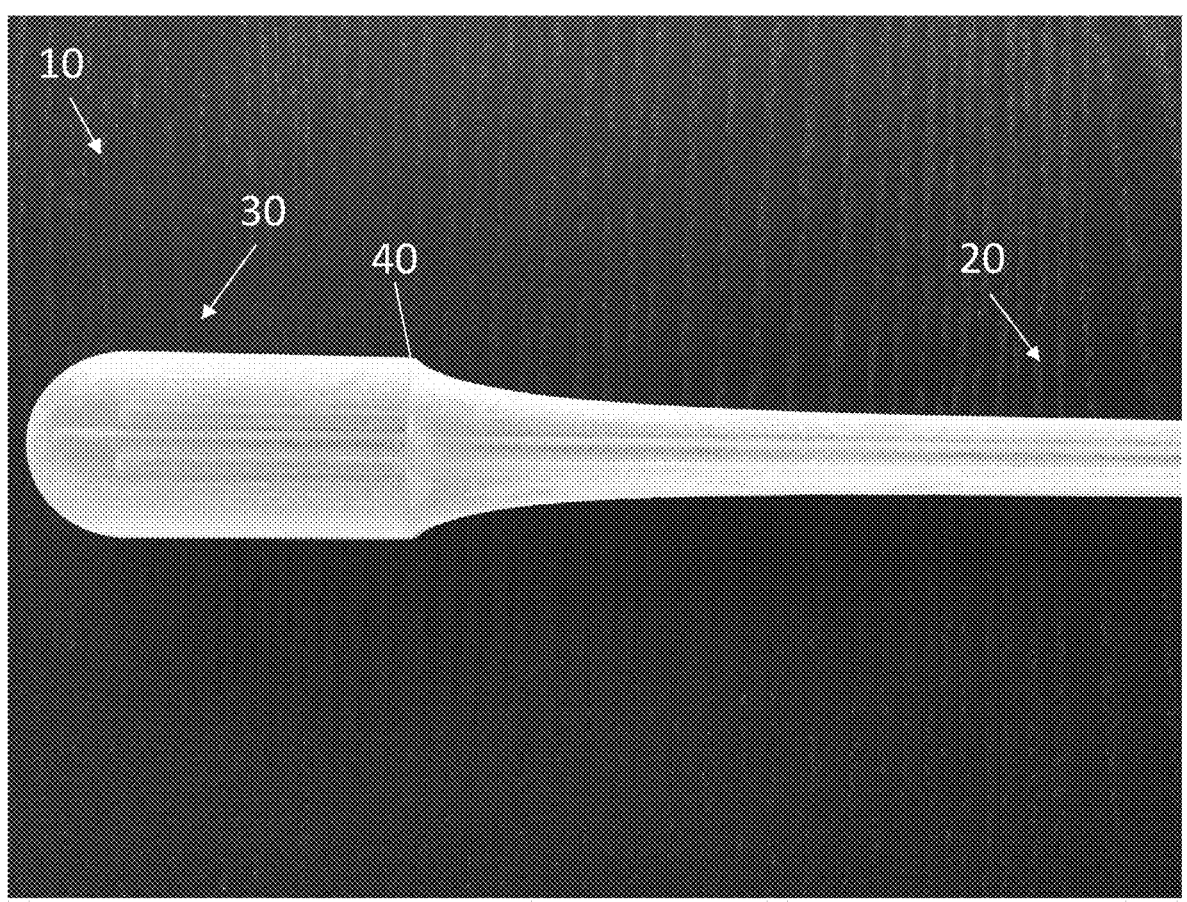
FIG. 1 is an exemplary illustration of an applicator of the invention, which is in an aligned configuration with respect to the two semi-cylindrical bodies. The image illustrates the distal end of the aligned applicator. Due of the translucence of this illustration, the central single-ended channel, and the two peripheral parallel tracks that allow for the two semi-cylindrical bodies to slide past each other, are visible. In this illustration, the distal end is itself tapered to a round (smooth) extremity, and the distal end has approximately the same diameter as the tapering point.
Figure 2:
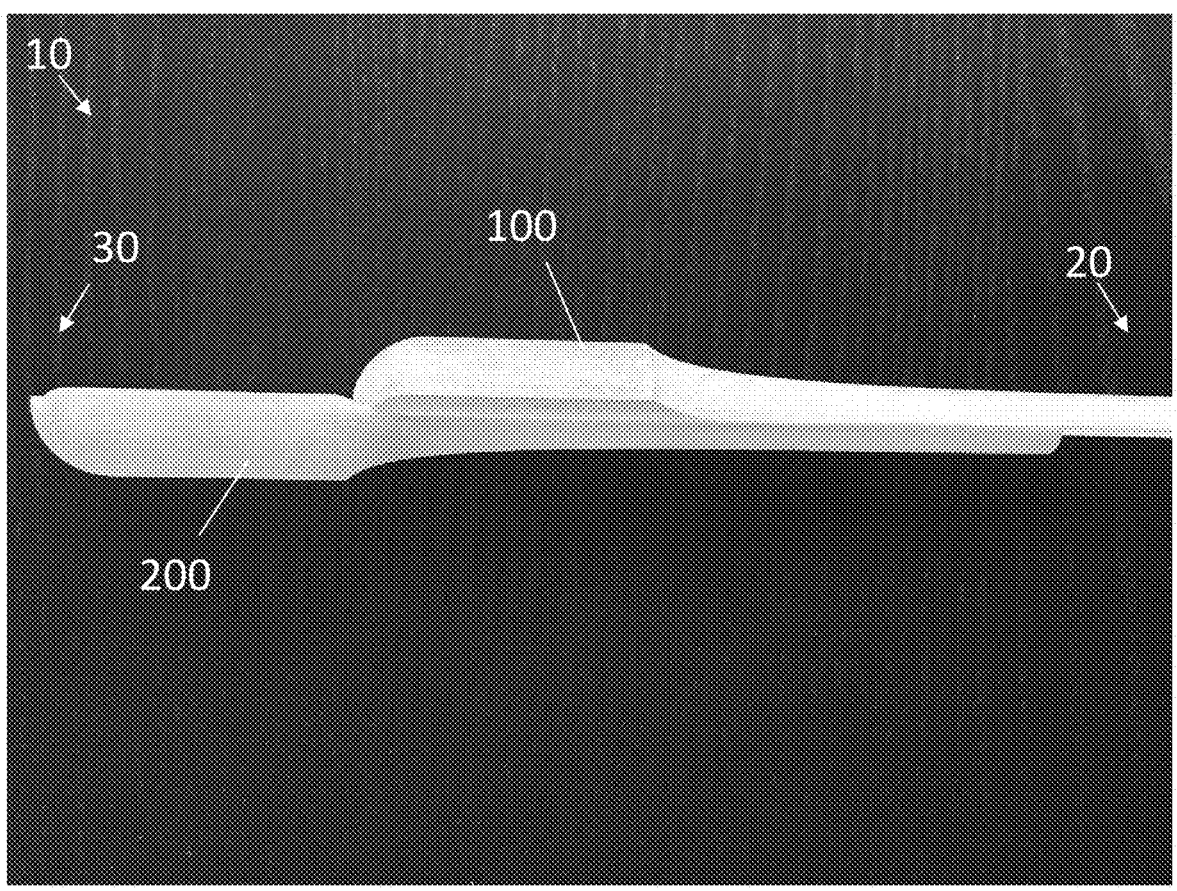
FIG. 2 is an exemplary side-view illustration of an applicator of the invention, which is in a non-aligned configuration with respect to the two semi-cylindrical bodies.
Figure 3:
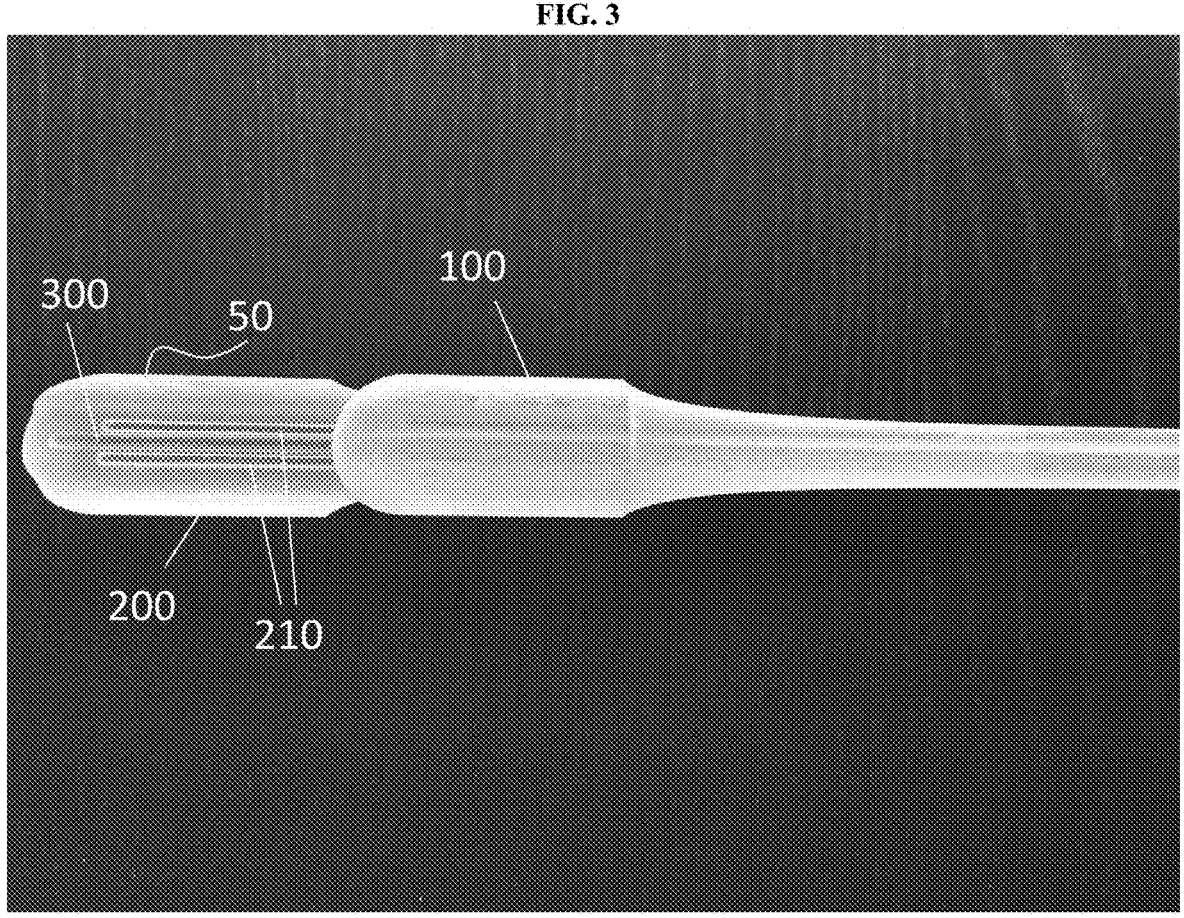
FIG. 3 is an exemplary top-view illustration of an applicator of the invention, which is in a non-aligned configuration with respect to the two semi-cylindrical bodies.
Figure 4:
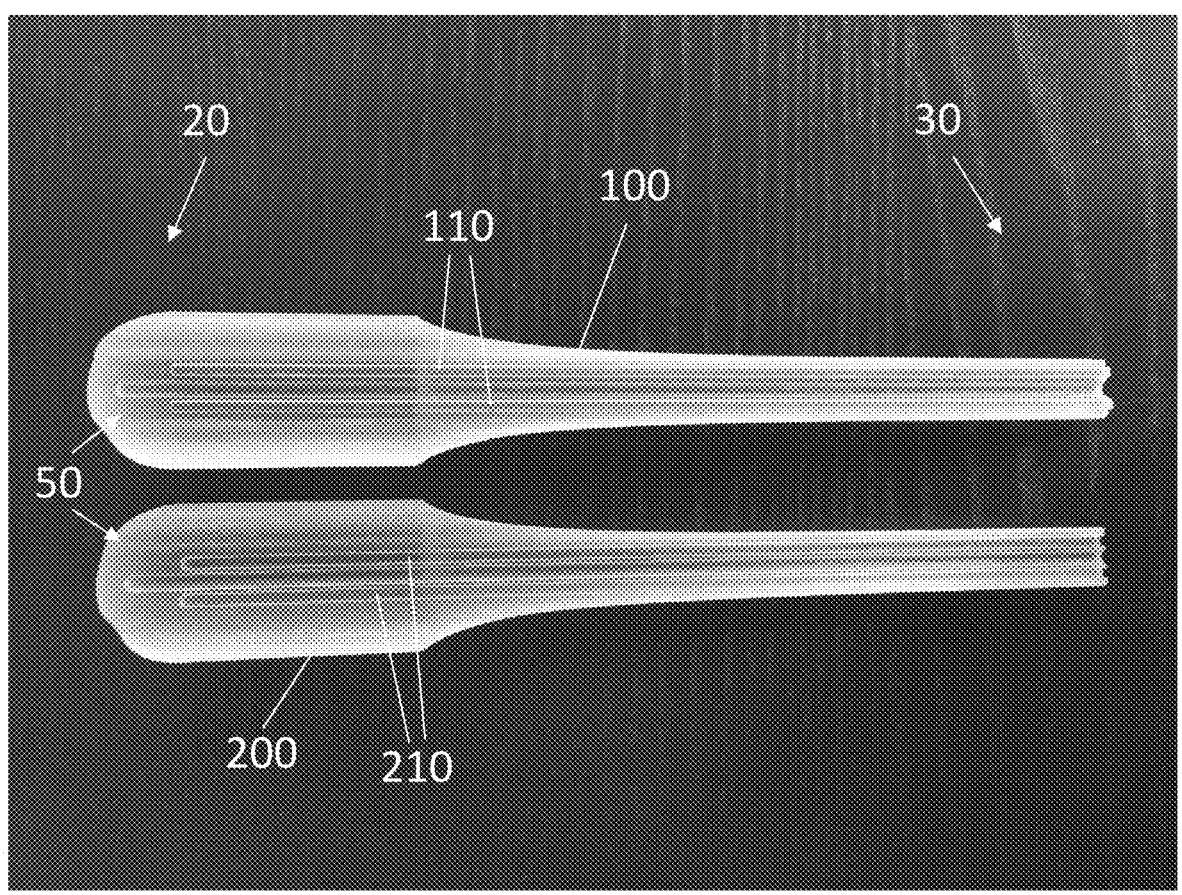
FIG. 4 is an exemplary illustration of two semi-cylindrical bodies side by side, in a non-aligned (and disengaged) configuration.

The invention relates in part to the unexpected discovery of a tapered applicator 10, which can be used to deliver high-dose-rate vaginal brachytherapy to a female patient's vagina following hysterectomy. A non-limiting tapered two-piece vaginal brachytherapy applicator is described. In certain embodiments, applicator 10 comprises two separate interlocking pieces 100 and 200, which form a tapered cylinder when secured together in its final locked position. In certain embodiments, a central channel 300 for HDR catheter delivery is surrounded by integrated alignment tracks comprised of curved surfaces to minimize radiation leakage. In certain embodiments, the two-piece design enables a two-step insertion, such that the base half is first inserted to the apex followed by gently guiding the top half over interlocking parallel alignment tracks until it is securely locked into position. Due to the tapered design of the applicator, at no point during the positioning does its diameter in the region of the introitus exceed that of a standard 3 cm cylinder, and when secured in its final position, the diameter is approximately 50% reduced.

In certain embodiments, once inserted through the female patient's vaginal opening (or introitus), the applicator of the invention causes less physical discomfort to the female patient than currently available applicators. In other embodiments, the applicator is used in a female patient whose vaginal apex is larger in diameter than her vaginal introitus.

High-dose rate (HDR) brachytherapy is a type of internal radiation therapy that delivers radiation directly to a tumor site over a short period of time. Brachytherapy treatment for endometrial cancer following hysterectomy generally involves insertion of a plastic cylinder through the patient's vaginal opening. The applicator itself is not radioactive, but is attached to a radioactive feed that will place a single radioactive pellet temporarily into the central channel of the applicator by a computer-controlled machine. The radioactive pellet will travel to the previously placed applicator via a guide catheter connecting the computer controlled machine and applicator on the end of a computer controlled guidewire. This computer controlled machine and guidewire are controlled remotely, and the radioactive pellet is delivered to the end of the applicator after the applicator has been placed in a technique known as "remote afterloading." Standard cylinders have a fixed applicator diameter and length and are inserted into the patient's vaginal canal in a single step.

However, utilizing such cylinders to deliver brachytherapy treatment limits target volume dose parameters due to applicator diameter restrictions. In patients with an apex (or vaginal vault) that is larger in diameter than the introitus, physicians are limited in applicator size due to the vagina's narrow opening or decreased elasticity. This may result in physical limits to amount and/or positioning of the radiation source, and may cause suboptimal treatment.

Efforts have been made to develop custom vaginal applicators (such as intra-vaginal balloon applicators, acrylic mold applicators, and other stereolithography applicators). However, these applicators do not allow for a template based treatment approach. Moreover, the currently available applicators still cause significant discomfort in the patients. The present invention is, in one aspect, a rigid plastic applicator maximizing comfort for women with a narrow vaginal introitus, guaranteeing reproducibility of radiation dosimetry with a non-deformable and rigid cylinder shape at the vaginal apex, and optimizing radiation dosimetry at the applicator-patient interface by allowing for the largest cylinder diameter at the vaginal apex.

In order to optimize uniform radiation dose, an applicator should be in direct contact with the vaginal mucosa. When limited to the diameter of the introitus, air pockets will likely exist around the apex of the applicator. Unfortunately, these air pockets reduce radiation dose, resulting in underdosing and increased risk of vault recurrence. Dose escalation is a possible solution to improve coverage, but this creates a risk of increased toxicity for the patient. A possible alternative would involve using larger vaginal cylinders. But, importantly, the patient may not tolerate the larger applicator size, hampering patient satisfaction and treatment compliance.

As described herein, the present invention provides a tapered but rigid plastic applicator, which provides several advantages over the devices of the prior art. In certain embodiments, it maximizes comfort for female patients with a narrow vaginal introitus. In other embodiments, it guarantees reproducibility of radiation dosimetry with a non-deformable and rigid cylinder shape at the vaginal apex. In yet other embodiments, it optimizes radiation dosimetry at the applicator-patient interface by allowing for the largest cylinder diameter at the vaginal apex.

In one aspect, to improve applicator fit and patient comfort, a novel applicator 10 was designed using 3D print technology. The applicator was designed as two hemicylindrical parts 100 and 200 (see FIGS. 1-4). The first hemi-cylindrical part 100 can be inserted first into the patient's vagina, and the second hemi-cylindrical part 200 can slide along the first part via alignment tracks formed from a complementary indentation 110 and a complementary projection 210. Inserting the applicator in two parts results in improved comfort compared to a standard fixed-diameter vaginal cylinder. In certain embodiments, at no point in the introitus does the cross-sectional area of the applicator exceed that of a standard 3 cm diameter applicator. In certain embodiments, the cross-sectional area of the applicator comprises a diameter smaller than that of a standard 3 cm diameter applicator. In certain embodiments, the cross-sectional area of the applicator comprises, for example, a smaller standard 2.3 cm diameter or a smaller standard 2.6 cm diameter. In certain embodiments, the cross-sectional area of the applicator is about 2.0 cm, 2.0-2.3 cm, 2.2-2.5 cm, 2.4-2.7 cm, 2.6-3.9 cm, 2.8-3.2 cm, 3.0-3.3 cm, or 3.2-3.5 cm. In certain embodiments, the applicator of the present invention is therapeutically similar to that of a non-tapered diameter cylinder, for example a non-tapered 2.3 cm diameter, 2.6 cm diameter or 3 cm diameter.

In a non-limiting illustrative embodiment, the applicator is designed as a 3 cm (diameter)×6 cm (length) cylinder continuous with a cylindrical stem that immediately begins to taper to a diameter of 1.5 cm. In certain embodiments, the cylindrical stem is 15 cm in length, resulting in a total applicator length of 21 cm. A central channel 300, of 2-4 mm diameter, such as 3 mm diameter, for a catheter to deliver high-dose-rate brachytherapy, is designed from the base of the applicator to 5 mm below the apex. Parallel alignment tracks formed from complementary indentation 110 and complementary projection 210 surround central channel 300, allowing a secure fit as second hemicylindrical part 200 is slid on top of first hemicylindrical part 100. In certain embodiments, when second part 200 is fully slid onto first part 100, the end stem contains threads for a metal guide to screw into, thereby locking the central catheter in place. In other embodiments, the applicator incorporates curved surfaces from the central channel to minimize radiation leakage.

Rapid prototyping printing service manufacturers have introduced materials that are both International Standard ISO-10993 rated and United States Pharmacopeia (USP) Class VI approved, meeting standards for biocompatibility. In certain embodiments, a choice of 3D print material for the applicator is PC-ISO (polycarbonate-ISO), a thermoplastic polycarbonate, which in its raw state is biocompatible (ISO 10993 USP Class VI) and can be gamma sterilized, ethylene oxide sterilized and/or STERRAD® sterilized (using low-temperature, hydrogen peroxide gas plasma technology). PC-ISO is commonly used in food and drug packaging and medical device manufacturing because of the material's strength and medical compatibility. PC-ISO has high flexure modulus and tensile strength properties, and is a common choice for many medical applications. Moreover, PC-ISO has been evaluated for its radiation attenuation properties and its suitability for applicator manufacturing (Cunha, et al., 2015, J. Appl. Clin. Med. Phys. 16(1):5168), as well as other medical applications such as ankle-foot orthoses, lumbar cages, and bone screw linking devices. Other USP Class VI and ISO-10993 compliant materials include, but not limited to, Sustarin C MG (acetal or polyoxymethylene copolymer), Propylux HS/HS2 (heat stabilized polypropylene), SustaPPO MG (Noryl HNA055; modified polyphenylene oxide), Sustason PSU MG (polysulfone), SustaPEEK MG (PEEK; polyether ether ketone), Ketron PEEK LSG (Life Science Grade), SustaPEI MG (Ultem; amorphous polyetherimide), and Sustason PPSU (Radel R; polyphenolsulfone).

Compositions

The invention provides a gynecological brachytherapy applicator 10 comprising an elongated cylindrical body having a proximal end 20, a distal end 30, and a longitudinal axis 60 that connects the proximal and distal ends of the cylindrical body.

Figure 5:
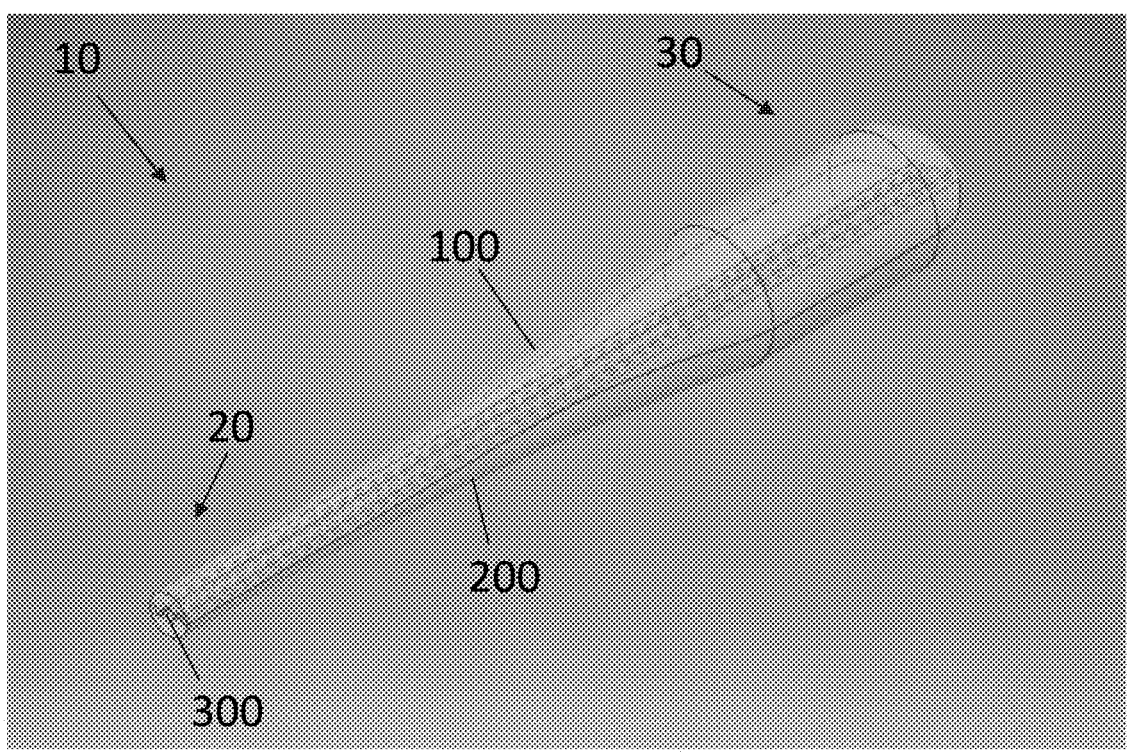
FIG. 5 is an exemplary see-through illustration of an applicator of the invention, which is in an aligned configuration with respect to the two semi-cylindrical bodies. The image illustrates in dotted lines the central single-ended channel and the two peripheral parallel tracks that allow for the two semi-cylindrical bodies to slide past each other. The image further illustrates the opening of the single-opening channel in the proximal end of the cylindrical body.
Figure 6:
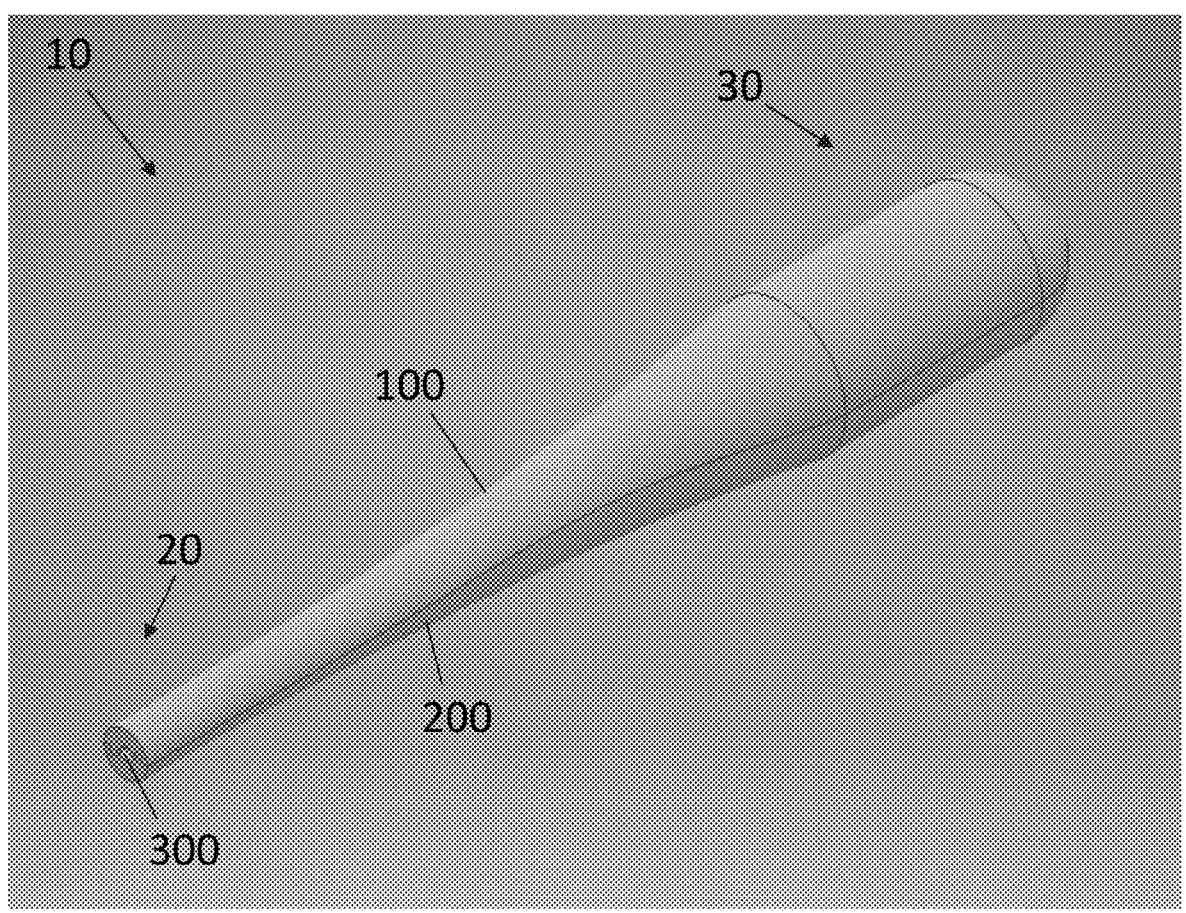
FIG. 6 is the corresponding solid illustration of the view shown in FIG. 5.

In certain embodiments, the cylindrical body is sectioned along a plane spanning the longitudinal axis 60 into first 100 and second 200 hemi-cylindrical bodies, wherein the first 100 and second 200 hemi-cylindrical bodies can slide longitudinally with respect to each other along the sectioning plane 50. In other embodiments, the applicator is in an "aligned" configuration ("aligned applicator") when the proximal ends of the first 100 and second 200 hemi-cylindrical bodies are aligned and the distal ends of the first 100 and second 200 hemi-cylindrical bodies are aligned. Non-limiting illustrations of such aligned configurations are provided in FIG. 1 and FIGS. 5-6. Non-limiting illustrations of non-aligned configurations are provided in FIGS. 2-4. Non-limiting illustrations of disengaged configurations (where the two hemi-cylindrical bodies are not in contact) are provided in FIG. 4.

In certain embodiments, the surfaces of the first and second hemi-cylindrical bodies along the sectioning plane 50 are indented such that, in an aligned applicator, a single-opening channel 300 is formed in the cylindrical body. In other embodiments, channel 300 is situated longitudinally along the cylindrical body and has its single opening to the proximal end of the elongated cylindrical body. Non-limiting illustrations of such channel are provided in FIGS. 1 and 5. In yet other embodiments, one or more channels are situated throughout the cylindrical body in the mid-coronal plane of the applicator. The arrangement of catheters provide sufficient dwell positions distributed evenly throughout the applicator to provide appropriate lateral dose dispersion at the wide vaginal apex.

In certain embodiments, in the aligned applicator, the diameter of the distal end is larger than the diameter of the proximal end. In other embodiments, in the aligned applicator, the cylindrical body has a tapering point along the longitudinal axis, wherein the diameter of the cylindrical body between the distal end and the tapering point is approximately the same, and the diameter of the cylindrical body gradually decreases between the tapering point and the proximal end.

It should be noted that the description of diameters of the distal end 30 and the proximal end 20 does not take into account any additional tapering that may result in one or two extremities of smaller diameter. For example, in FIG. 1 distal end 30 is tapered to a round (smooth) extremity, and, as used in this application, the diameter of distal end 30 refers to the diameter of distal end 30 in the absence of this extremity tapering. So, as used in this application, the diameter of distal end 30 in FIG. 1 is considered to be approximately the same as the diameter of the tapering point 40 therein. Likewise, as used in this application, the diameter of proximal end 20 refers to the diameter of proximal end 20 in the absence of any extremity tapering.

In certain embodiments, at least one selected from proximal end 20 and the distal end is further tapered. In other embodiments, at least one selected from proximal end 20 and distal end 30 is further tapered to a round extremity.

In certain embodiments, the single-opening channel 300 is parallel to the longitudinal axis. In other embodiments, single-opening channel 300 spans the longitudinal axis. In yet other embodiments, single-opening channel 300 allows for insertion of a catheter into the cylindrical body. In other embodiments, more than one single-opening 300 channel is present in the applicator.

In certain embodiments, single-opening channel 300 ends about 2-8 mm, 2.5-7.5 mm, 3-7 mm, 3.5-6.5 mm, 4-6 mm, or 4.5-5.5 mm, such as for example 5 mm away from the distal end 30 of the cylindrical body.

In certain embodiments, applicator 10 comprises a material that is resistant to radiation and/or is thermoplastic and/or sterilizable. In other embodiments, applicator 10 comprises a polymer. In yet other embodiments, the polymer is at least one selected from the group consisting of fluoropolymer, natural latex, synthetic latex, polyurethane, polycarbonate, silicone, acetal or polyoxymethylene copolymer, heat stabilized polypropylene, polyphenylene oxide, polysulfone, polyether ether ketone, amorphous polyetherimide, polyphenolsulfone, and any combinations thereof. In yet other embodiments, the polymer comprises a thermoplastic polycarbonate, such as but not limited to PC-ISO.

In certain embodiments, the surfaces of the first 100 and second 200 hemi-cylindrical bodies along sectioning plane 50 comprise a set of complementary indentations and projections that allow for first 100 and second 200 hemi-cylindrical bodies to slide longitudinally with respect to each other along the sectioning plane 50. In other embodiments, first hemi-cylindrical body 100 comprises two indentations along the sectioning plane 50 and second hemi-cylindrical body 200 comprises two complementary projections 210 along the sectioning plane 50. In yet other embodiments, first hemi-cylindrical body 100 comprises indentations along sectioning plane 50 as well as at the apex at the distal end of the cylindrical body above central channel 300, and second hemi-cylindrical body 200 comprises complementary projections along sectioning plane 50 as well as at the apex at the distal end of the cylindrical body above central channel 300. In yet other embodiments, first hemi-cylindrical body 100 comprises a projection and an indentation along sectioning plane 50 and second hemi-cylindrical body 200 comprises a complementary indentation 110 and a complementary projection 210, respectively, along the sectioning plane 50. Non-limiting illustrations of such complementary indentations 110 and projections 210 (such as tracks) are provided in FIGS. 1-5.

In certain embodiments, in the aligned applicator the diameter of distal end 30 is approximately the diameter of a patient's vaginal apex. In other embodiments, in the aligned applicator the diameter of distal end 30 is approximately 2-4 cm, for example 3 cm.

In certain embodiments, in the aligned applicator the diameter of proximal end 20 is approximately the diameter of a patient's vaginal introitus. In other embodiments, in the aligned applicator the diameter of proximal end 20 is approximately 1-3 cm, for example 1.5 cm.

In certain embodiments, the distance between distal end 30 and the tapering point 40 is about 3-9 cm, 3.5-8.5 cm, 4-8 cm, 4.5-7.5 cm, 5-7 cm, or 5.5-7.5 cm, for example 6 cm.

In certain embodiments, the distance between proximal end 20 and the tapering point 40 is about 10-20 cm, 11-19 cm, 12-18 cm, 13-17 cm, or 14-16 cm, for example 15 cm.

In certain embodiments, the diameter of the aligned applicator decreases approximately uniformly between tapering point 40 and proximal end 20. In other embodiments, the diameter of the aligned applicator does not decrease uniformly between tapering point 40 and proximal end 20.

In certain embodiments, first 100 and second 200 hemi-cylindrical bodies are secured to each other in the aligned applicator, so that the hemi-cylindrical bodies can no longer slide longitudinally with respect to each other along sectioning plane 50. In other embodiments, first 100 and second 200 hemi-cylindrical bodies are secured to each other using a linking part comprising a fastener, lock, pin, nail, clip, screw, straps, magnets, or various interlocking alignment tracks.

In certain embodiments the first 100 and second 200 hemi-cylindrical bodies are secured using a threaded locking mechanism such as, for example a nut or cap, that securely, reproducibly and reversibly holds the two bodies together and does not allow for longitudinal sliding of the hemi-cylindrical bodies relative to each other.

In certain embodiments there is one or more raised edges, lips, handles or the like on each of the first 100 and second 200 hemi-cylindrical body to allow the user to slide unlocked and unsecured hemi-cylindrical bodies with one hand or two hands. In certain embodiments, when inserted in the patient, hemi-cylindrical bodies 100 and 200 only have the proximal end accessible to the user. In such embodiments, hemi-cylindrical bodies 100 and 200 are unlocked and slid longitudinally with manipulation only of the proximal end of the applicator. In certain embodiments, the applicator is lubricated using any suitable lubricant as understood in the art. In certain embodiments, the one or more raised edges, lips, handles or the like is positioned at the proximal end of each hemi-cylindrical body and allows for secure and facilitated manipulation of the hemi-cylindrical bodies including maneuvering longitudinally relative to each other.

In certain embodiments, the linking part is attached to the cylindrical body in the vicinity of its proximal end. In other embodiments, the linking part is attached to the radioactive feeding device.

Methods

The invention provides a method of providing intravaginal brachytherapy to a female patient suffering from endometrial cancer. In certain embodiments, the invention provides methods for providing therapy to a patient suffering from other primary or secondary malignancies of the vagina, involving the vagina, or with potential to spread to the vagina, for example uterine or endometrial cancer, cervical cancer, vaginal cancer, vulvar cancer, vaginal melanoma, and ovarian cancer. In certain embodiments, the method comprises applying radiation to at least a section of vaginal tissue of the female patient using at least one gynecological brachytherapy applicator of the invention. In other embodiments, the patient is human.

Figure 7:
FIG. 7 comprises a sagittal view of a female illustrating a non-cylindrical shape to the post-hysterectomy vagina, without a cylinder in situ.
Figure 7:
Figure 8:
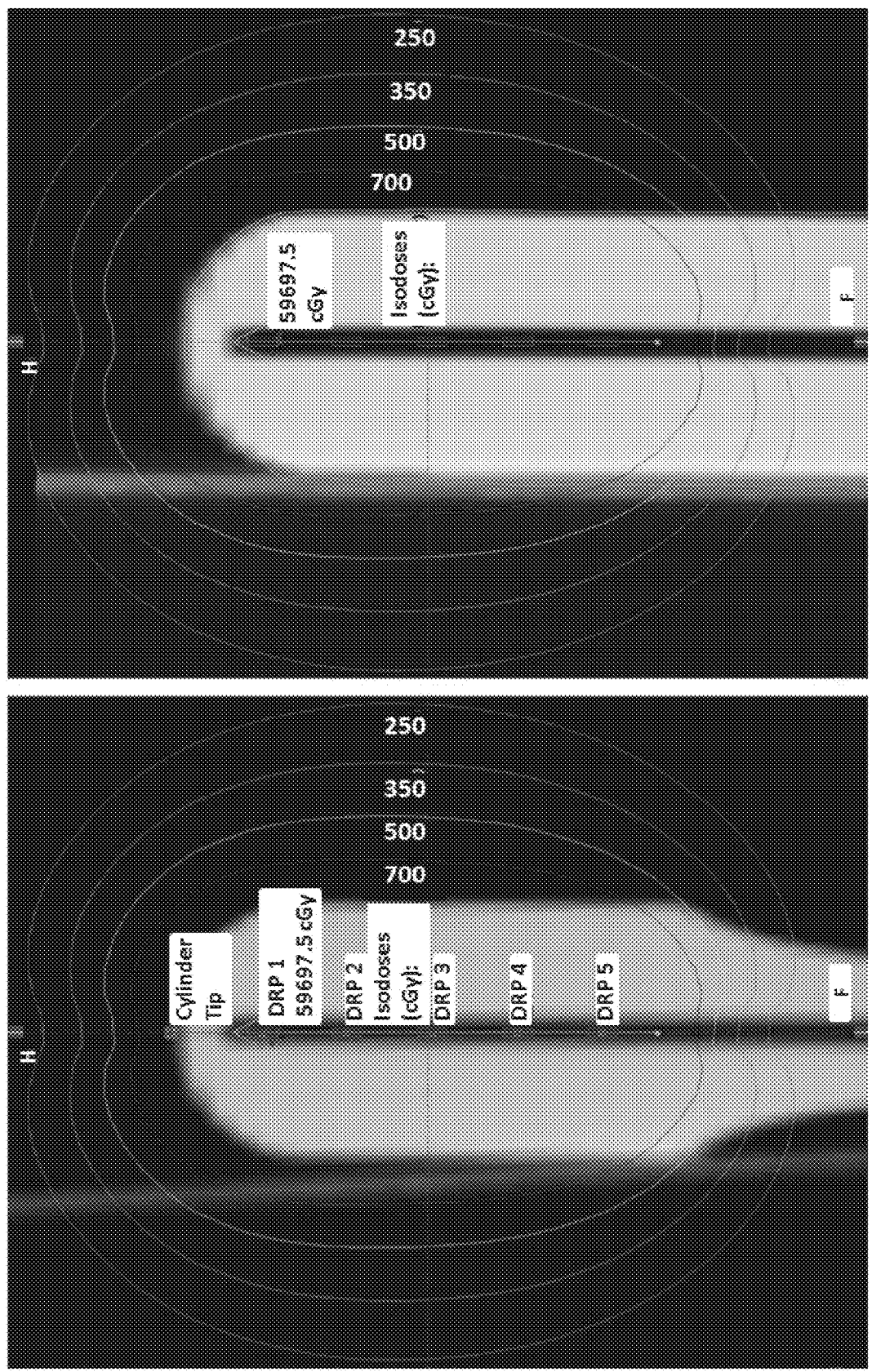
FIG. 8 is an exemplary illustration comparing the dosimetric properties of the tapered applicator to a standard 3 cm diameter cylinder. A library template plan was applied, corresponding to a prescription of 700 cGy delivered to 5 mm depth from the surface of 3 cm cylinder to the tapered applicator. The dose distribution surrounding the tapered applicator is depicted and compared with that of a standard 3 cm diameter cylinder in FIG. 1. The distribution at the apex is identical between the two applicators. In the region of the taper, in certain embodiments, the mucosal surface dose resulting from the tapered design can theoretically exceed that of a standard cylinder. In the template depicted, with an activated treatment length of 4 cm (5 activated dwell positions, 1 cm apart), the dose measured at the surface of the tapered region was very low. The dose fall off in the region of the taper surface ranged from 500 cGy at the start of the taper to 250 cGy at 1 cm in the caudal direction. Therefore, for an activated treatment length of up to 4 cm, the dose distribution surrounding the novel applicator is nearly identical to that of a standard 3 cm cylinder and results in likely negligible differences in surface dose at the taper.

In certain embodiments, the method comprises inserting into a female patient at least one gynecological brachytherapy applicator of the invention, wherein applicator 10 is first unaligned. For example, in certain embodiments, the method comprises inserting into a patient an applicator 10 of the present invention wherein the first 100 and second 200 hemi-cylindrical bodies are not aligned (shown in FIG. 2). The distal end of the first hemi-cylindrical body 100 is inserted into a subject to an appropriate position as understood by one skilled in the art. In certain embodiments, the second hemi-cylindrical body 200 is then slid along the one or more interlocking complementary indentations 110 and projections 210 until first 100 and second 200 hemicylindrical bodies are aligned, and wherein applicator 10 is positioned within the patient in an aligned configuration (shown in FIGS. 1 and 7). In certain embodiments, a catheter is inserted into central channel 300 of applicator 10 and a therapy is administered to a subject in need thereof. In certain embodiments, the applicator is placed using, for example a guidewire. In some embodiments, one or more catheters are placed into one or more central channels using, for example, one or more guidewires. In certain embodiments the therapy is radiotherapy, for example brachytherapy and is administered to a patient in need thereof according to techniques described herein and/or according to other techniques as understood by a skilled artisan. In certain embodiments, the methods of the present invention apply brachytherapy to a subject in need thereof, while minimizing radiation leakage and maximizing patient comfort Definitions As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in cell culture, molecular genetics and materials science are those well-known and commonly employed in the art.

The following abbreviations are used herein: EBRT, external beam radiotherapy, VBT, vaginal brachytherapy.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "instructional material" includes a publication, a recording, a diagram, or any other medium of expression that may be used to communicate the usefulness of the compositions and/or methods of the invention. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; and/or instructions for use of the compositions.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Every combination of components described or exemplified can be used to practice the invention, unless otherwise stated. Specific names of compounds are intended to be exemplary, as it is known that one of ordinary skill in the art can name the same compounds differently.

Although the description herein contains many embodiments, these should not be construed as limiting the scope of the invention but as merely providing illustrations of some of the presently preferred embodiments of the invention.

All references throughout this application (for example, patent documents including issued or granted patents or equivalents; patent application publications; and non-patent literature documents or other source material) are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. In general the terms and phrases used herein have their art-recognized meaning, which can be found by reference to standard texts, journal references and contexts known to those skilled in the art. Any preceding definitions are provided to clarify their specific use in the context of the invention.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

All materials were used without further preparation unless indicated otherwise below. In certain embodiments, the applicator can be prepared using a prototyping printing service, such as Stratasys Direct Manufacturing, from a material such as, but not limited to, PC-ISO.

Example 1

A clinical study is conducted to assess patient comfort with an illustrative vaginal applicator of the invention. In one aspect, patients are fit with different applicators and their comfort is assessed with a Likert-scale based survey.

In a non-limiting example, patients can be fitted with (1) a standard "small" cylinder with applicator diameter <3.0 cm (2) a standard 3.0 cm-diameter applicator; and (3) an applicator of the invention. Patients are then assessed using a survey with questions such as:

| | |
|---|---|
| I felt pain with insertion | 0 1 2 3 4 5 6 7 8 9 10 |
| I felt pressure with insertion: | 0 1 2 3 4 5 6 7 8 9 10 |

-continued

| | |
|---|---|
| I felt burning with insertion: | 0 1 2 3 4 5 6 7 8 9 10 |
| I felt stress with insertion: | 0 1 2 3 4 5 6 7 8 9 10 |
| I felt my vagina was being stretched: | 0 1 2 3 4 5 6 7 8 9 10 |

Example 2

A clinical study is conducted to assess in vivo dosimetry with an illustrative vaginal applicator of the invention. In one aspect, patients are fit with the illustrated tapered applicator and MRI and/or CT images are taken to assess dosimetry, fit, contact with mucosal surfaces and presence of air gaps.

Example 3

A dosimetric planning study to characterize and compare the dosimetric properties of the tapered applicator to a standard cylinder. A library template plan was applied, corresponding to a prescription of 700 cGy delivered to 5 mm depth from the surface of 3 cm cylinder to the tapered applicator. The dose distribution surrounding the tapered applicator is depicted and compared with that of a standard 3 cm diameter cylinder in FIG. 1. The distribution at the apex is identical between the two applicators. In the region of the taper, the mucosal surface dose resulting from the tapered design could theoretically exceed that of a standard cylinder. In the template depicted, with an activated treatment length of 4 cm, the dose measured at the surface of the tapered region was very low. The dose fall off in the region of the taper surface ranged from 500 cGy at the start of the taper to 250 cGy at 1 cm in the caudal direction. Therefore, for an activated treatment length of up to 4 cm, the dose distribution surrounding the novel applicator is nearly identical to that of a standard 3 cm cylinder and results in likely negligible differences in surface dose at the taper.

Example 4

A clinical study is performed to show improvement in vaginal health for women who would be unable to undergo treatment with a standard 3 cm non-tapered cylinder. To do this, women who underwent treatment with a non-tapered lower diameter cylinder are compared to women who underwent treatment with the tapered applicator. Immediate and long term vaginal health is compared objectively and subjectively. Vaginal stenosis (narrowing of the vagina) after treatment is compared between the two techniques.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A gynecological brachytherapy applicator comprising an elongated cylindrical body having a proximal end, a distal end, and a longitudinal axis that connects the proximal and distal ends of the elongated cylindrical body, wherein the elongated cylindrical body is sectioned along a plane spanning the longitudinal axis into a first hemi-cylindrical body and a second hemi-cylindrical body,
  wherein the first hemi-cylindrical body comprises a proximal end and a distal end,
  wherein the second hemi-cylindrical body comprises a proximal end and a distal end,
  wherein the first and second hemi-cylindrical bodies are adapted and configured to slide longitudinally with respect to each other along the sectioning plane;
wherein the surfaces of the first and second hemi-cylindrical bodies along the sectioning plane comprise an indentation, wherein with the proximal ends of the first and second hemi-cylindrical bodies aligned and the distal ends of the first and second hemi-cylindrical bodies aligned, an aligned elongated cylindrical body is formed to provide at least one single opening channel in the aligned elongated cylindrical body
  wherein the at least one single-opening channel is positioned longitudinally along the aligned elongated cylindrical body and comprises a single opening to the proximal end of the aligned elongated cylindrical body;
wherein, in the aligned elongated cylindrical body,
(i) the diameter of the distal end of the aligned elongated cylindrical body is larger than the diameter of the proximal end of the aligned elongated cylindrical body, and
(ii) the aligned elongated cylindrical body has a tapering point along the longitudinal axis,
  wherein the diameter of the aligned elongated cylindrical body between the distal end and the tapering point of the aligned elongated cylindrical body is about the same, and
  wherein the diameter of the aligned elongated cylindrical body gradually decreases between the tapering point and the proximal end of the aligned elongated cylindrical body.

2. The applicator of claim 1, wherein the at least one single-opening channel is parallel to the longitudinal axis of the aligned elongated cylindrical body.

3. The applicator of claim 2, wherein the at least one single-opening channel spans the longitudinal axis of the aligned elongated cylindrical body.

4. The applicator of claim 1, wherein the at least one single-opening channel is adapted and configured for insertion of a catheter into the aligned elongated cylindrical body.

5. The applicator of claim 1, wherein the at least one single-opening channel ends about 3-7 mm away from the distal end of the aligned elongated cylindrical body.

6. The applicator of claim 1, wherein the applicator comprises a material that is resistant to radiation or is thermoplastic.

7. The applicator of claim 6, wherein the applicator comprises a polymer, wherein the polymer is at least one selected from the group consisting of fluoropolymer, natural latex, synthetic latex, polyurethane, polycarbonate, silicone, acetal or polyoxymethylene copolymer, heat stabilized polypropylene, polyphenylene oxide, polysulfone, polyether ether ketone, amorphous polyetherimide, polyphenolsulfone, and any combinations thereof.

8. The applicator of claim 7, wherein the polymer comprises a thermoplastic polycarbonate.

9. The applicator of claim 1, wherein the surfaces of the first and second hemi-cylindrical bodies along the sectioning plane comprise a set of complementary indentations and projections that allow for the first and second hemi-cylindrical bodies to slide longitudinally with respect to each other along the sectioning plane.

10. The applicator of claim 9, wherein the first hemi-cylindrical body comprises two indentations along the sectioning plane and the second hemi-cylindrical body comprises two complementary projections along the sectioning plane.

11. The applicator of claim 9, wherein the first hemi-cylindrical body comprises a projection and an indentation along the sectioning plane and the second hemi-cylindrical body comprises a complementary indentation and a complementary projection, respectively, along the sectioning plane.

12. The applicator of claim 1, wherein the diameter of the distal end of the aligned elongated cylindrical body is from about 2 cm to about 4 cm.

13. The applicator of claim 1, wherein the diameter of the proximal end of the aligned elongated cylindrical body is from about 1 cm to about 3 cm.

14. The applicator of claim 1, wherein the distance between the distal end and the tapering point of the aligned elongated cylindrical body is from about 4 cm to about 8 cm.

15. The applicator of claim 1, wherein the distance between the proximal end and the tapering point of the aligned elongated cylindrical body is from about 10 cm to about 20 cm.

16. The applicator of claim 1, wherein, in the aligned applicator configuration, the first and second hemi-cylindrical bodies are secured to each other in the aligned elongated cylindrical body, and the hemi-cylindrical bodies do not slide longitudinally with respect to each other along the sectioning plane.

17. The applicator of claim 16, wherein the first and second hemi-cylindrical bodies are secured to each other using a part comprising a fastener, lock, pin, nail, clip, screw, strap, or various interlocking alignment tracks, wherein the part is attached to the elongated cylindrical body in the vicinity of the proximal end of the elongated cylindrical body.

18. The application of claim 1, wherein at least one selected from the proximal end and the distal end of the elongated cylindrical body is further tapered to form an extremity having a corresponding smaller diameter.

19. The application of claim 18, wherein at least one selected from the proximal end and the distal end of the elongated cylindrical body is further tapered to a round extremity.

20. A method of administering intravaginal brachytherapy to a female patient in need thereof, the method comprising:
  applying radiation to at least a section of vaginal tissue of the female patient using a gynecological brachytherapy applicator comprising an elongated cylindrical body having a proximal end, a distal end, and a longitudinal axis that connects the proximal and distal ends of the elongated cylindrical body,
    wherein the elongated cylindrical body is sectioned along a plane spanning the longitudinal axis into a first hemi-cylindrical body and a second hemi-cylindrical body,
      wherein the first hemi-cylindrical body comprises a proximal end and a distal end,
      wherein the second hemi-cylindrical body comprises a proximal end and a distal end,
      wherein the first and second hemi-cylindrical bodies are adapted and configured to slide longitudinally with respect to each other along the sectioning plane;

wherein the surfaces of the first and second hemi-cylindrical bodies along the sectioning plane comprise an indentation, wherein with the proximal ends of the first and second hemi-cylindrical bodies aligned and the distal ends of the first and second hemi-cylindrical bodies aligned, an aligned elongated cylindrical body is formed to provide at least one single opening channel in the aligned elongated cylindrical body,
 wherein the at least one single-opening channel is positioned longitudinally along the aligned elongated cylindrical body and comprises a single opening to the proximal end of the aligned elongated cylindrical body;
wherein, in the aligned elongated cylindrical body,
(i) the diameter of the distal end of the aligned elongated cylindrical body is larger than the diameter of the proximal end of the aligned elongated cylindrical body, and
(ii) the aligned elongated cylindrical body has a tapering point along the longitudinal axis,
wherein the diameter of the aligned elongated cylindrical body between the distal end and the tapering point of the aligned elongated cylindrical body is about the same, and
wherein the diameter of the aligned elongated cylindrical body gradually decreases between the tapering point and the proximal end of the aligned elongated cylindrical body.

* * * * *